US009026189B2

(12) United States Patent
Garcia et al.

(10) Patent No.: US 9,026,189 B2
(45) Date of Patent: May 5, 2015

(54) ELECTRODE SENSOR ASSEMBLY FOR ELECTRORETINOGRAPHY AND PATTERN ELECTRORETINOGRAPHY

(71) Applicants: Alberto Gonzalez Garcia, Pine Brook, NJ (US); Donald E. Lepone, Pine Brook, NJ (US)

(72) Inventors: Alberto Gonzalez Garcia, Pine Brook, NJ (US); Donald E. Lepone, Pine Brook, NJ (US)

(73) Assignee: Diopsys, Inc., Pine Brook, NJ (US)

( * ) Notice: Subject to any disclaimer, the term of this patent is extended or adjusted under 35 U.S.C. 154(b) by 0 days.

(21) Appl. No.: 13/678,725

(22) Filed: Nov. 16, 2012

(65) Prior Publication Data

US 2014/0142409 A1    May 22, 2014

(51) Int. Cl.
*A61B 5/0496* (2006.01)

(52) U.S. Cl.
CPC ....... *A61B 5/0496* (2013.01); *A61B 2562/0209* (2013.01)

(58) Field of Classification Search
CPC ..................................... A61B 5/0496
USPC .................. 600/383, 391, 392, 558
See application file for complete search history.

(56) References Cited

U.S. PATENT DOCUMENTS

| 4,763,660 | A | * | 8/1988 | Kroll et al. ................... | 600/391 |
| 5,154,174 | A | * | 10/1992 | Hawlina ........................ | 600/383 |
| 5,772,591 | A | * | 6/1998 | Cram ............................ | 600/383 |
| 7,496,400 | B2 | * | 2/2009 | Hoskonen et al. ............ | 600/544 |
| 8,118,752 | B2 | * | 2/2012 | Hetling et al. ............... | 600/558 |
| 8,172,459 | B2 | * | 5/2012 | Abreu .......................... | 374/208 |
| 2005/0096513 | A1 | * | 5/2005 | Ozguz et al. ................. | 600/301 |
| 2011/0237921 | A1 | * | 9/2011 | Askin et al. .................. | 600/377 |
| 2012/0253163 | A1 | * | 10/2012 | Afanasewicz et al. ........ | 600/383 |

* cited by examiner

*Primary Examiner* — Lee S Cohen
(74) *Attorney, Agent, or Firm* — Levisohn Berger LLP

(57) ABSTRACT

A multilayer electrode sensor assembly for electroretinography and pattern electroretinography formed as a thin strip to fit under a lower eyelid and contain an electrode in line with the pupil of an eye with signals detected carried through an integrally formed thin conductive strip to a terminal to be connected to an electrical conductor for carrying such signals to an analyzer.

19 Claims, 3 Drawing Sheets

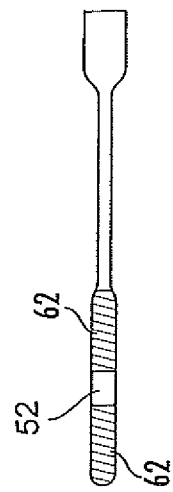 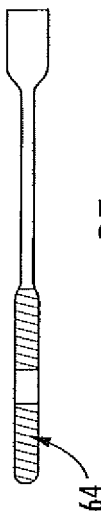 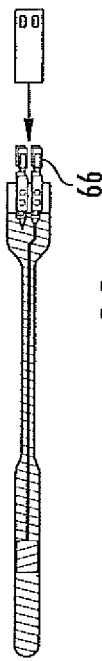 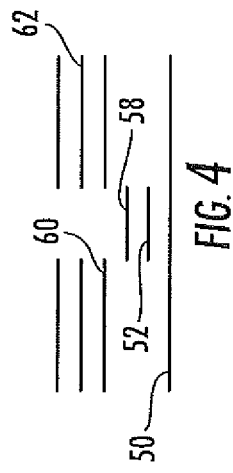
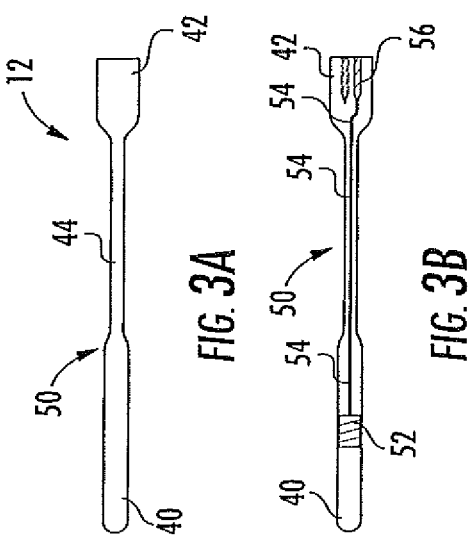 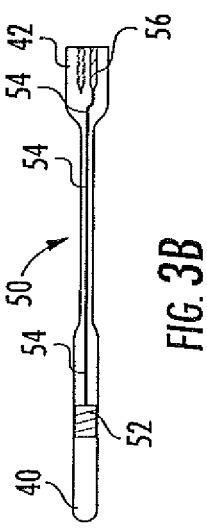 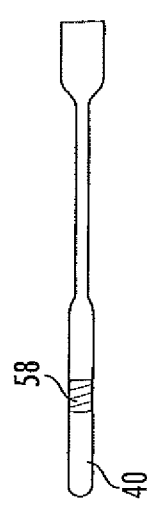 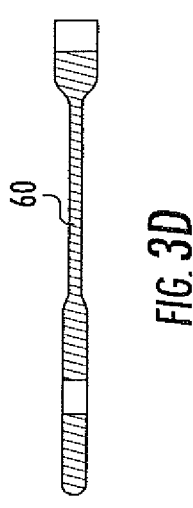

ELECTRODE SENSOR ASSEMBLY FOR ELECTRORETINOGRAPHY AND PATTERN ELECTRORETINOGRAPHY

BACKGROUND OF THE INVENTION

This invention relates to an electrode sensor assembly for electroretinography and pattern electroretinography.

Determining the functioning of the retina is significant in diagnosing, assessing and monitoring the progression of dysfunction due to disease or trauma. Electroretinography (ERG) and Pattern Electroretinography (pERG) are systems which use different visual stimuli including patterns to stimulate the eye and causes the retina to generate responses, and resulting signals are analyzed. An analysis of signal amplitude and latency leads to monitoring and diagnosis of retinal health.

Microelectrical signals are generated in the retina during ERG and pERG testing and are analyzed by standard diagnostic equipment and techniques. pERG vision testing is a well established technology with a broad foundation of scientific support. This invention permits significantly improved test administration.

A significant aspect of such systems is the ability to detect the electrical signals generated in the retina for analysis. A variety of approaches have been tried to locate electrodes close enough to the retina which allow for detection of electrical signals without materially interfering with the test itself. These prior art systems generally are clumsy and cumbersome and detract from patient comfort and cooperation.

There are contact lens electrode systems which require placing a contact lens on the eye and suitable electrodes within or attached thereto which then are attached to leads carrying electrical signals from the retina. There are other systems in which individual circular electrodes are adhesively attached around the eye, close to the eyelid, with leads hanging therefrom. The individual electrode placements around the eye is unwieldy, somewhat inefficient and not very secure. Additionally, some of these prior art systems are sensitive to eye movement, thereby creating noise which interferes with the accuracy of the pERG or ERG test. The plurality of leads dangling from the eye interferes with appropriate utilization of these electrodes for reliable collection of data during a pERG or ERG procedure or otherwise interferes with patient comfort sufficient so that the retinal analysis becomes impaired.

An object of this invention is to provide an improved electrode sensor assembly for ERG, pERG and other retina exam procedures in order to monitor the biopotential on tissue.

Another object of this invention is to provide such an electrode sensor assembly which is easy to place on the patient, located close enough to receive electrical signals and easy to remove after a test is complete.

Another object of this invention is to provide such an assembly which minimizes interference with the testing, minimizes discomfort of the patient and reduces undesirable noise.

Yet another object of this invention is to provide such an assembly which does not directly touch the eye but is capable of suitably receiving electrical signals and thereby minimizes discomfort of the patient as well as interference with the efficacy of the test.

Yet another object of this invention is to provide such an assembly which is disposable to reduce the possibility of contamination and cross-contamination, is easily placed and located where desired and easily and quickly removable after a test is complete.

Another object of this invention is to improve the collection of data during a pERG or ERG procedure utilizing standard equipment to analyze the collected data so that the present invention can be used by personnel already trained in the field.

Still another object of this invention is to facilitate greater widespread use of pERG or ERG vision testing.

Other objects, advantages and features of this invention will become more apparent from the following description.

SUMMARY OF THE INVENTION

In accordance with the principles of this invention, the above objects and features are provided for an electrode sensor which has a multilayer assembly. The multilayer assembly has an adhesive backed electrode and thin conductor strip shaped and sized to fit on the skin below the lower eyelid, tucked under the lower eyelashes, to be easily attached and removed.

An electrode is formed within the strip and located below the eye. A conductor is integrally formed within the strip and connects to the electrode to carry electrical signals generated in the retina to a miniature connector or terminal. The conductive strip of this invention is suitable for ERG and pERG, as well as other electroretinographic procedures which generate electrical pulses and signals within the retina responsive to triggering events.

The conductive strip, preferably, is disposable, further ensuring cleanliness and minimizing potential cross contamination and infection. Many prior art electrodes are used and reused, which is undesirable.

The electrode sensor assembly serves as a lid sensor and works cooperatively with reference sensors placed on the patient's face to collect electrical signal information for processing and diagnostic analysis. The shape of the lid sensors are narrow, elongated, easily placed on the skin below the lower eyelid, tucked under the lower eye lashes conforming to the skin below the lower eyelid and comprise an electrode surrounded by adhesive material to attach the lid sensor to the skin.

The conductive strip may have a thin middle section, a micro-connector on one end and an encapsulated electrode contained therein which detects and senses signals from the retina.

The lid sensor is formed of a plurality of layers comprising a bottom plastic or white vinyl layer covered with a conductive material forming the electrode. An insulating layer covers the electrode and an adhesive layer is formed on either side of the electrode with a removable medical tape liner covering the adhesive layer.

In use, the medical tape liner is removed from the adhesive layer, and the conductive strip is positioned on the skin below the lower eyelid. The strip has a visible indication to locate the electrode in line with the pupil. The conductive strip or sensor is placed close to the eyelid margin below the eyelashes so that the electrical signals collected in the retina are collected by the sensor.

It will be understood that the data collected is analyzed in the standard manner, but the collection of such data as well as patient comfort and cooperation is improved.

BRIEF DESCRIPTION OF THE DRAWINGS

FIGS. 3a-3g are top perspective views of the lid sensor of this invention showing the multilayer formation of the lid sensor assembly.

FIG. 4 is an exploded sectional view showing the layers of the lid sensor.

DETAILED DESCRIPTION OF THE PREFERRED EMBODIMENT

Figure 1:
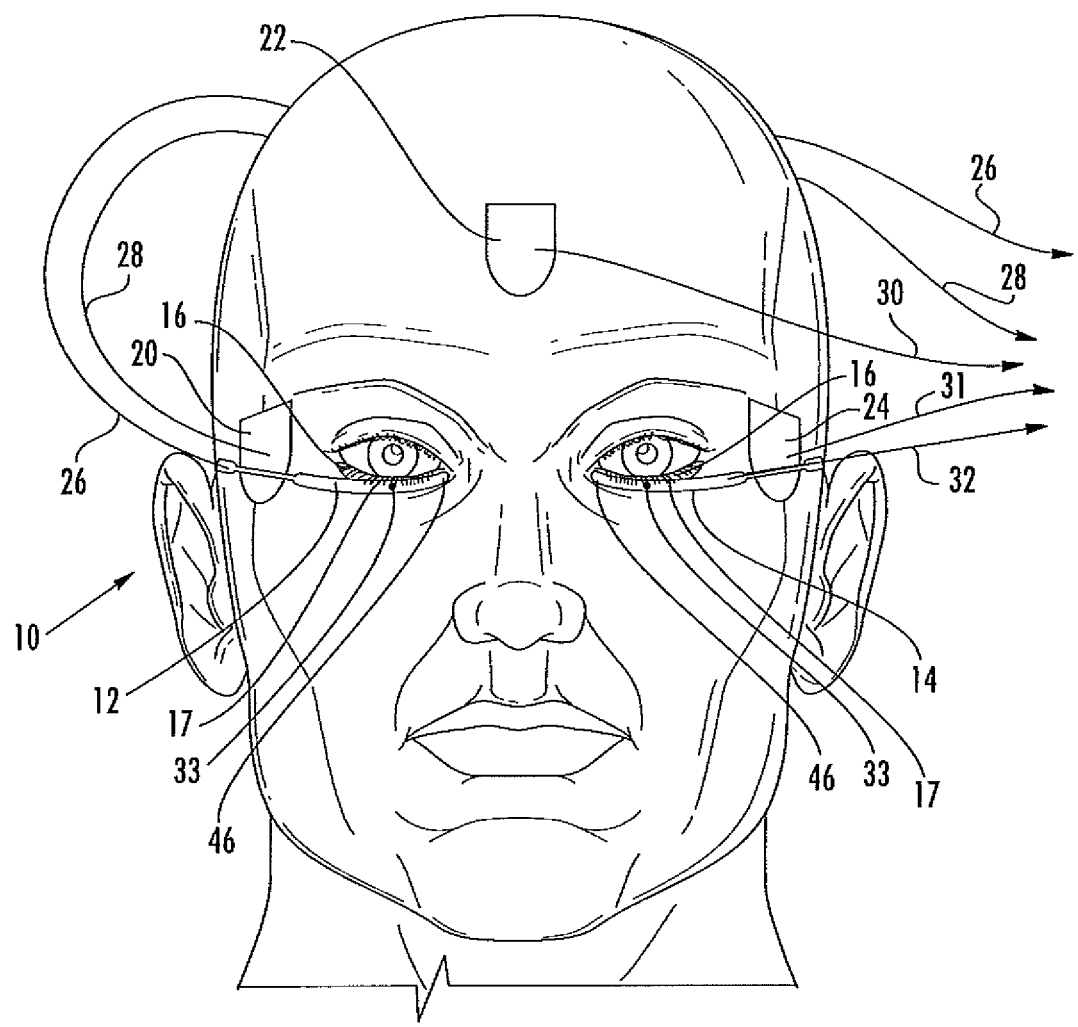
FIG. 1 is a front plan view of a face showing placement of the lid sensors of this invention as well as reference sensors used in pERG.

FIG. 1 is a front plan view of the front of a face 10 showing sensors 12 and 14, which are the sensors used for pERG or ERG set up and testing. The present invention is directed to the right and left lower lid sensors 12 and 14, respectively, which are elongated and thin, placed on the skin (no number) on the lower eyelid 16, with lower eyelashes 17 covering the sensors to pick up retinal signals. The signals from the lid sensors 12 and 14 are utilized in conjunction with signals in OD Reference, Ground and OS Reference sensors, 20, 22 and 24, respectively, with sensors 20 and either side of the temple and sensor 22 located centrally above the eyebrows.

With suitable pERG testing, signals are generated at the lid sensors 12 and 14. Reference sensors are placed in an area that is distant from any response generated by the retina. The references serve as controls for the pERG test. The generated signals from the procedure are carried on conductors 26 for OD lid sensor 12, 28 for OD reference sensor 20, 30 for ground sensor 22, 31 for OS reference sensor 24, and 32 for OS lid sensor 14. Conductors 26-32 are connected to suitable terminals in analyzing equipment. A visible indication of where the electrode on the lid sensor 14 is located may be designated, for instance, with a dot 33 to assist to properly locate the electrode in line and below the pupil of the eye.

Figure 2:
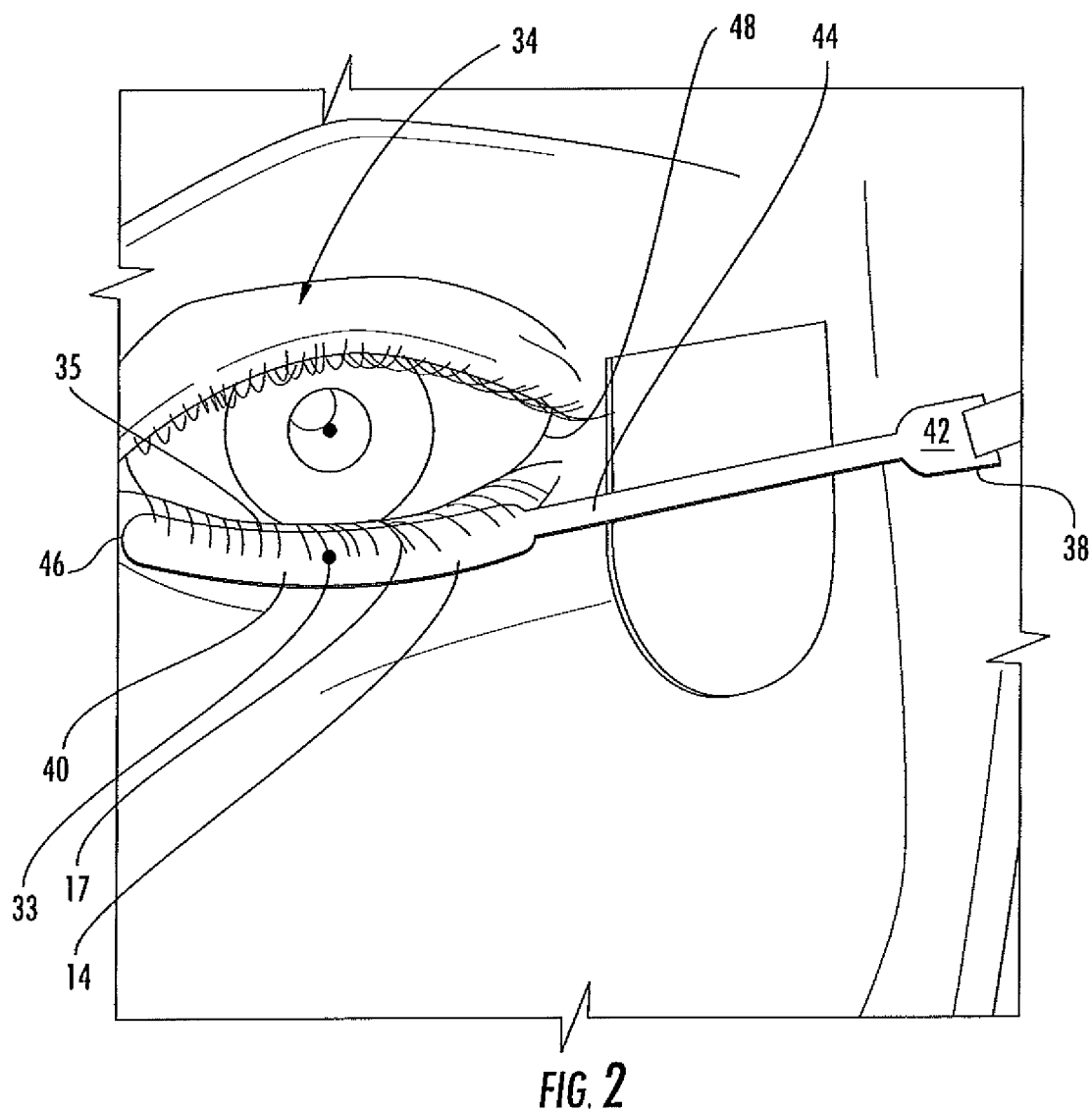
FIG. 2 is a front plan view of the left eye of a patient with the lid sensor of this invention in place.

FIG. 2 is a close up front plan view of the left eye 34 of a patient, showing the lid sensor 14 placed on the skin just below the lower eyelid 35 and tucked under lower eyelashes 17. The lid sensor 14 comprises an embedded electrode (see FIG. 3) connected to an embedded electrical conductor with the conductor carried through to a micro-connector 38 at the end of lid sensor 14.

The lid sensor comprises a first section 40 having the electrode and a portion of the conductor (see FIGS. 3a-3g) as a second section 42 and an intermediate section 44. The sensors 12 and 14 are elongated and thin and are sized and shaped to extend from the inner corner 46 of the eye to the outer corner 48 edge of the eye as shown.

The lid sensor 14 is attached to the skin below the eyelid with an adhesive material revealed when a tape liner is removed from covering the adhesive layer. The lid sensor 14 is placed as indicated in FIG. 2 with the electrode directly below and in line with the pupil and signals are generated and carried through to the conductor 38. An indication of where the electrode in the lid sensor 14 is located may be designated, for instance, where the dot 33 is located to assist in properly locating the electrode in line and below the pupil of the eye.

FIGS. 3a-3g shows a lid sensor (12 or 14) which comprises a vinyl or other plastic soft thin base layer 50 having an enlarged left or first section 40, a thinner middle section or intermediate section 44 and a right or second section 42. The silhouette of the lid sensor is shown in FIG. 3a and the plastic or vinyl layer forms the base layer 50.

FIG. 3b shows the application and formation of the electrodes and conductors within the lid sensor 12 or 14. A conductor material such as silver ink is used to form electrode 52 located in section 40, being substantially square in shape and connected to a conductor 54 extending from electrode 52 through the intermediate section 44 to the right or second section 42. The conductor 54 is formed of a thin extended length of conductive material which connects to a terminal 56 in the right section 42.

The location of electrode 52 is designated on the visible side of the lid sensors 12 and 14 so as to locate the electrode 52 directly in line with the pupil of the eye. The larger the electrode 52 the more signal it can pick up and carry through conductor 54 to terminal 56.

FIG. 3c shows the application of a conductive gel 58 substantially square in shape and slightly larger than electrode 52 which further assists the carrying of electrical signals from electrode 52 to conductor 54.

FIG. 3d is a view of the silhouette of the lid sensors similar to FIGS. 3a-3c, in which an insulating dielectric layer 60 is placed on top of the prior layers deposited on base layer 50 (FIG. 3a). This insulating or dielectric layer may be formed of a blue dielectric ink and prevents stray noise from being picked up in the conductor 54. The dielectric layer is shown on top of conductor 54 but it could also be deposited on top of electrode 52.

FIG. 3e shows the application and location of adhesive material 62 on either side of electrode 52 in first section 40. The adhesive material enables the electrode to remain in place with the adhesive material securing the lid sensor of this invention to the skin just below the lower eyelid.

It is intended that only the left end 40 be attached to the skin with the balance of the lid sensor near but not being attached to the skin because additional adhesive material may be difficult to remove. On the other hand, it is within the ordinary skill of one in the art to select the type of adhesive material so that greater adhesion could be obtained with lesser material and the electrode size could be larger and adhesive material could be carried in the middle section 44, if desired. Terminal or connector 56 may be a microconnector and may comprise female contacts Nicomatic 14106-12.

FIG. 3f shows the placement of a tape liner 64 on top of the left section 40 of the lid sensor which, when removed, exposes the adhesive material 62 to enable the lid sensor to be attached to the skin under the lower lid as shown in FIGS. 1 and 2.

FIG. 3g shows a contact 66 connected to connector 54 which carries the electrical signals picked up by electrode 52 to electrical wires 26 and 32.

Adhesive material 62 surrounds electrode 52.

The height of sections 40 and 42 is greater than the height of section 44. Electrode 52 is substantially equal in height to first section 40.

FIG. 4 is an exploded sectional view through the lid sensor showing the multilayer assembly to form the skin sensor. The first base layer 50 is the polyester or plastic layer upon which is then deposited the electrode material 52 of a silver ink which is then covered by a conductive gel of silver chloride. The electrode material forms electrode 52 and conductor 54. Any suitable conductive material may be utilized. Thereafter, an insulating or dielectric material 60 is deposited on top of the lower layers and an adhesive layer 62 is then placed on the dielectric layer, which is then (with the electrode 52) covered by a removable medical tape 64.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

The invention claimed is:

1. An electrode sensor for detecting signals emanating from a retina of the eye of a patient, said signals being generated upon stimulation of the retina,
    said electrode sensor comprising a multilayer assembly comprising a base layer, an electrode deposited on said base layer and a conductor deposited on said base layer connected to said electrode,
    said electrode sensor comprising a first elongated section, said electrode being located on said first elongated section, said first elongated section being sized and shaped to extend from an inner corner of an eye to an outer corner edge of an eye to be secured to skin below a lower eyelid of a patient,
    said electrode sensor comprising a second section, said second section comprising a connector,
    said conductor being located in an intermediate section of said sensor between said first and second sections, said conductor integrally formed with said electrode,
    said multilayer assembly comprising an adhesive layer to attach said electrode sensor to said skin below said lower eyelid.

2. An electrode sensor according to claim 1, further comprising a dielectric layer formed on top of said conductor to minimize noise in said conductor.

3. An electrode sensor according to claim 1, wherein said multilayer assembly comprises a conductive gel deposited on top of said electrode.

4. An electrode sensor according to claim 1, wherein said adhesive layer comprises adhesive material located adjacent to said electrode in said first section.

5. An electrode sensor according to claim 4, wherein said adhesive material is located on both sides of said electrode in said first section.

6. An electrode sensor according to claim 1, wherein said electrode sensor has an elongated and thin silhouette.

7. An electrode sensor according to claim 1, wherein said connector is fixedly attached to said conductor.

8. An electrode sensor according to claim 1, wherein said multilayer assembly comprises a medical tape liner on top of said adhesive layer.

9. An electrode sensor according to claim 1, wherein at least a portion of said intermediate section is smaller in height than either said first or second sections.

10. An electrode sensor according to claim 1, wherein the height of said electrode is substantially equal to the height of said first section.

11. An electrode sensor according to claim 1, wherein said base layer comprises a thin plastic material.

12. An electrode sensor according to claim 1, wherein said electrode sensor is thin and flexible.

13. An electrode sensor according to claim 1, wherein said electrode sensor comprises visible locating means to locate said electrode substantially to be in line with the pupil of the eye.

14. An electrode sensor according to claim 13, wherein said visible locating means is visible to the naked eye.

15. An electrode sensor according to claim 1, wherein said electrode and said conductor comprises a conductive ink material.

16. An electrode sensor according to claim 15, further comprising a dielectric ink deposited on top of said conductor.

17. An electrode sensor according to claim 1, wherein said connector is a microconnector.

18. An electrode sensor according to claim 1, wherein only said first section comprises adhesive material.

19. An electrode sensor according to claim 1, wherein said electrode and said conductor are integrally formed and comprise the same layer of said multilayer assembly.

* * * * *